United States Patent [19]

Switzer et al.

[11] 4,371,431

[45] Feb. 1, 1983

[54] PHOTOELECTROCHEMICAL GENERATION OF THALLIUM(III)

[75] Inventors: Jay A. Switzer, Placentia; Eric L. Moorehead, Diamond Bar, both of Calif.

[73] Assignee: Union Oil Company of California, Brea, Calif.

[21] Appl. No.: 310,310

[22] Filed: Oct. 9, 1981

[51] Int. Cl.$^3$ .................... C25B 3/00; C25B 5/00
[52] U.S. Cl. .................... 204/59 R; 204/78; 204/79; 204/80; 204/157.1 R; 429/111
[58] Field of Search .................... 204/59 R, 78–80, 204/157.1 R; 429/111

[56] References Cited

U.S. PATENT DOCUMENTS

| | | | |
|---|---|---|---|
| 3,048,636 | 8/1962 | Grinstead | 260/586 |
| 3,436,409 | 4/1969 | Hill et al. | 260/348.5 |
| 3,479,262 | 11/1969 | MacLean et al. | 204/80 |
| 3,641,067 | 2/1972 | Kruse | 260/348.5 |
| 4,144,147 | 3/1979 | Jarrett et al. | 429/111 |
| 4,215,182 | 7/1980 | Ang et al. | 429/111 |
| 4,262,066 | 4/1981 | Brenneman et al. | 429/111 |

OTHER PUBLICATIONS

M. S. Wrighton, "Photoelectrochemical Conversion of Optical Energy to Electricity and Fuels", *Accounts of Chemical Research*, vol. 12, pp. 303–310 (1979).
M. S. Wrighton, "Photochemistry", *Chemical and Engineering News*, vol. 57, Sep. 3, 1979, pp. 29–37 and 42–47.
A. J. Bard, "Photoelectrochemistry", *Science*, vol. 207, pp. 139–144 (1980).
S. N. Frank and A. J. Bard, "Semiconductor Electrodes, 12, Photo-assisted Oxidations and Photoelectrosynthesis at Polycrystalline TiO$_2$ Electrodes," *Journal of the American Chemican Society*, vol. 99, pp. 4667–4675 (1977).

*Primary Examiner*—R. L. Andrews
*Attorney, Agent, or Firm*—Dean Sandford; Gregory F. Wirzbicki; Robert A. Franks

[57] ABSTRACT

Thallium(III) is produced in solution using a photoelectrochemical cell which has an externally electrically interconnected semiconductor photoelectrode and counter electrode. A conductive solution containing thallium(I) is placed in the cell and a flow of current generated by exposing the photoelectrode to actinic radiation, thereby oxidizing the thallium.

In another embodiment, a thallium(III) solution is produced by mixing a solution containing thallium(I) with a particulate semiconductor, introducing an oxygen-containing gas into the mixture, and exposing the mixture to actinic radiation.

The produced thallium(III) can be reacted with organic compounds, for example with compounds containing at least one carbon-carbon double bond to form epoxides, concurrently reducing thallium. Continuous production can be obtained by recycling the reduced thallium by photoelectrochemical oxidation to thallium(III).

35 Claims, No Drawings

PHOTOELECTROCHEMICAL GENERATION OF THALLIUM(III)

BACKGROUND OF THE INVENTION

1. Field of the Invention

The invention relates to the photoelectrochemical oxidation of thallium(I) to thallium(III) in solutions, and to the use of the thallium(III) in oxidation reactions with organic compounds.

2. Description of the Art

Thallium(III) has been found to be a very useful chemical oxidizing agent, having a reduction potential of 1.247 volts (versus the normal hydrogen electrode) for Reaction 1.

$$Tl^{+3} + 2e^- \rightarrow Tl^+ \qquad (1)$$

Use has been made of thallium(III) in a variety of organic synthesis schemes.

Organic compounds which can be reacted with thallium(III) include those which have an index of hydrogen deficiency greater than zero. This index is described by J. B. Hendrickson, D. J. Cram and G. S. Hammond, *Organic Chemistry*, Third Edition, McGraw-Hill, Inc., 1970, at pages 72-73 and 82-83, as the number of pairs of hydrogen atoms which must be removed from a saturated alkane to give the empirical formula of a subject compound. For a hydrocarbon, then, the index represents the total of the rings and multiple bonds in a molecule. For compounds containing heteroatoms, the following principles can be used to make the index application: (1) oxygen and sulfur atoms do not change the index; (2) each halogen atom is equivalent to one-half of a hydrogen atom pair; and (3) each nitrogen atom requires that the "reference" saturated alkane be considered as having one extra hydrogen atom (i.e., a formula of $C_nH_{2n+3}$).

A paper by Grinstead in *Journal of Organic Chemistry*, Vol. 26, pages 238-240 (1961), reported the oxidation of the olefins ethylene and 2-hexene by aqueous acidic solutions of thallium(III) to form carbonyl compounds and glycols or their esters. U.S. Pat. No. 3,048,636 to Grinstead also deals with this oxidation.

Reaction mechanism and kinetics for the oxidation of olefins by thallium(III) have been discussed in some detail by P. M. Henry in "Oxidizing Olefins by Pd(II) and Tl(III)," *Homogeneous Catalysis, ACS Advances in Chemistry Series*, Vol. 70, pages 126-154 (1968). The mechanism proposed for the oxidation, exemplified by that for ethylene, is as shown in Equations 2 and 3.

$$Tl^{+3} + CH_2=CH_2 + H_2O \xrightarrow{slow} HOCH_2CH_2Tl^{+2} + H^+ \qquad (2)$$

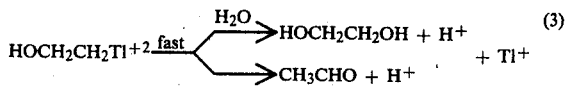

$$HOCH_2CH_2Tl^{+2} \xrightarrow{fast} \begin{array}{l} \xrightarrow{H_2O} HOCH_2CH_2OH + H^+ \\ \xrightarrow{\phantom{H_2O}} CH_3CHO + H^+ \end{array} + Tl^+ \qquad (3)$$

which explains the experimentally observed product mixture.

By utilizing weaker solvating media for the thallium(III), Kruse and Bednarski reported in *Journal of Organic Chemistry*, Vol. 36, pages 1154 and 1155 (1971), that the oxidation of olefins can be halted at an intermediate epoxide stage. For example, thallium triacetate, in a solvent composed of tetrahydrofuran, water and acetic acid (70, 20 and 10 percent by volume, respectively), oxidized propylene to form a mixture of 72 percent propylene oxide, 16 percent acetone and 12 percent 1-acetoxy-2-propanol. This reaction is the subject of U.S. Pat. No. 3,641,067 to Kruse.

In addition to the oxidation of olefins, many other organic reactions occur with thallium. A review by R. J. Ouellette, "Oxidation by Thallium(III)," Chapter 3 of *Oxidation in Organic Chemistry*, Part B, W. S. Trahanovsky, Ed., Academic Press, 1973, discusses work which has been done in the oxidation of steroids, oxidative rearrangement of chalcones, oxidative cleavage of cycloalkanes, oxidation of carbonyl compounds, oxidation of phenols, and reactions with silanes. Other interesting uses for thallium(III) include the conversion of benzene to phenol, wherein the reaction occurs as in Equations 4 and 5.

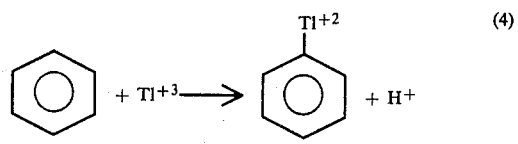

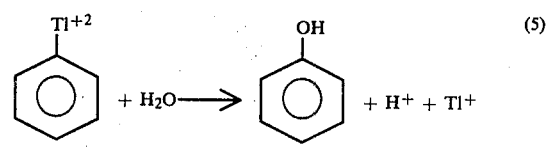

It is also possible to use a similar scheme to produce aniline, as shown by Equation 6.

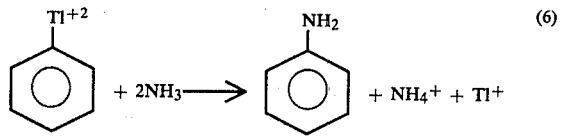

By using alkaline sulfides, thiophenols can be produced in a similar manner; haloaromatics can be prepared utilizing halide ions.

Unfortunately, however, regeneration of the thallium(III) from the thallium(I) formed in previously described reactions has presented a difficult problem. The thallic/thallous reduction potential is slightly positive of the oxygen/water couple (1.229 volts) of Equation 7,

$$O_2 + 4H^+ + 4e^- \rightarrow 2H_2O \qquad (7)$$

so that regeneration with molecular oxygen is not feasible. Attempts have been made to shift the reduction potential of the thallic/thallous couple (e.g., to 0.783 volts in 1 Formal hydrochloric acid), but such a shift is accompanied by a loss of oxidizing power for the thallium(III) species.

Chemical oxidation of thallous is, of course, possible with the very powerful agents such as chlorine gas and aqua regia, but these materials are objectionable as being somewhat difficult to handle (requiring expensive low-corrosion equipment), and cause the accumulation of undesirable materials in the system. A variety of methods for chemically oxidizing thallium(I) to thallium(III) with less objectionable materials have been developed.

Hirose et al., in U.S. Pat. No. 3,399,956, report a system for oxidizing thallium with oxygen, which involves an acidic aqueous medium containing chloride or bromide and an ion of a "redox metal" such as copper or iron. The metal ion is described as an "electron acceptor" when thallium(I) is converted to thallium-(III).

In U.S. Pat. No. 3,479,262, MacLean et al. describe an olefin oxidation process which includes a noble metal catalyzed reoxidation of thallium by electrochemically generated cerium(IV). Following Equations 8 and 9 describe anodic and cathodic electrode reactions, respectively, while Equation 10 shows the thallium reaction.

$$Ce^{+3} \longrightarrow Ce^{+4} + e^- \tag{8}$$

$$2H^+ + 2e^- \longrightarrow H_2 \tag{9}$$

$$2Ce^{+4} + Tl^+ \xrightarrow[\text{Aq. Acid}]{\text{Ru catalyst}} 2Ce^{+3} + Tl^{+3} \tag{10}$$

Also shown by MacLean et al. is the direct electrochemical generation of thallium(III) from thallium(I) in a divided cell, wherein thallium is not permitted to migrate into the cathode compartment, thereby avoiding deposition of thallium metal at the cathode. The electrochemical reactions are demonstrated for sulfuric acid-containing thallium solutions.

Other electrochemical systems for oxidizing thallium are shown in U.S. Pat. No. 3,486,992 to Frye and in U.S. Pat. No. 3,759,804 to LeBris et al.

U.S. Pat. No. 4,031,196 to Leonard is concerned with the regeneration of thallium(III) which has been used in the form of its isobutyrate for the oxidation of unsaturated organic compounds. The rather complex procedure includes air oxidation of an alkaline solution of thallium(I) isobutyrate at elevated temperatures, to produce a slurry of thallium(III) oxide which is removed. The remaining solution is treated with carbon dioxide, producing isobutyric acid which is extracted with a solvent. Isobutyric acid then dissolves the thallium(III) oxide, forming the initial oxidizing reagent.

Methods have been developed for chemically oxidizing thallium(I) in the presence of noble metals. These methods include those of Brill, as in U.S. Pat. No. 4,115,420 (oxidation with molecular oxygen in strongly acidic solution) and 4,115,421 (oxidation using an organic hydroperoxide). Rizkalla, in U.S. Pat. No. 4,058,542, oxidized thallium(I) using molecular oxygen in the presence of both a Group VIII metal and a heterocyclic tertiary amine "promoter," obtaining a higher product yield than that of Brill. A similar procedure is reported by Johnson, who used an alkali metal compound as promoter in U.S. Pat. No. 4,113,756 and an alkyl ammonium salt as a promoter in U.S. Pat. No. 4,192,814.

Thallium(III) has been generated by reaction with a perorganic acid (e.g., a mixture of acetic acid and hydrogen peroxide) in the presence of a manganese or ruthenium compound promoter, as shown by Walker in U.S. Pat. Nos. 4,135,051 and 4,226,790.

The described methods each suffer from one or more of the following disadvantages: (1) the requirement for relatively expensive chemical reagents which are irreversibly consumed during thallium oxidation; (2) the need for a separate thallium oxidation facility external to the equipment for organic compound oxidation by thallium(III); (3) gradual accumulation in the thallium solution of undesired by-products from the thallium oxidation reaction; and (4) a significant expenditure of thermal or electrical energy to accomplish thallium oxidation.

Due to the recent substantial increases in the cost of energy, considerable interest and research has been generated for the utilization of alternative energy sources, including the harnessing of solar radiation. An area which has received attention in connection with oxidation-reduction chemical reactions is that of photoelectrochemistry, wherein the interaction of photons with a suitable photoelectrode creates a flow of current in an electrochemical cell. Much of the reported efforts in this area has dealt with various forms of solar energy storage, e.g., the photoelectrolysis of water to form storable hydrogen, as in U.S. Pat. Nos. 3,925,212 to Tchernev; 4,011,149 and 4,090,933 to Nozik; 4,100,051 to Kilby; and 4,144,147 to Jarrett et al.

Other solar energy storage schemes include that of McKinzie et al. in U.S. Pat. No. 4,128,704 where, in one embodiment, water is dissociated into molecular oxygen and hydrogen ions at a photoanode under ultraviolet light, and a corresponding cathode reaction reduces cupric ions to metallic copper. The energy can be subsequently recovered by connecting an electrical load between the metallic copper electrode and a "reducing electrode" to which oxygen is supplied, and immersing both electrodes in an acid solution.

Another application for photoelectrochemistry which has had considerably less research attention is that of utilizing solar energy to conduct preparative chemical reactions. Many of the reported efforts in this field have been concerned with photocatalysis, wherein the activation energy to initiate an otherwise exoergic reaction is supplied photoelectrochemically. Several of these reactions have been summarized in a review by Bard, "Photoelectrochemistry," in Science, Vol. 207, pages 139–144 (1980) (which is incorporated herein by this reference), including the photo-Kolbe reaction, wherein decarboxylation proceeds according to Equation 11 in a photoelectrochemical cell.

$$2RCOOH \rightarrow R-R + 2CO_2 + 2H^+ + 2e^- \tag{11}$$

It is also possible to supply the required energy for endoergic chemical synthesis reactions, using a photoelectrochemical cell. This technique, which can be called "photoelectrosynthesis," has been utilized to produce amino acids from the reactants methane, ammonia, and water, as reported by Reiche and Bard in *Journal of the American Chemical Society*, Vol. 101, pages 3127–3128 (1979). Another paper by Frank and Bard in *Journal of the American Chemical Society*, Vol. 99, pages 4667–4675 (1977), describes the photooxidation of a number of organic and inorganic species, and suggests a method of synthesis involving indirect oxidation, e.g., photoelectrochemically oxidizing cerium(III) to cerium(IV), followed by reacting the cerium(IV) with a material, which simultaneously regenerates cerium(III).

It would be highly desirable to have available a method for photoelectrochemically generating the useful oxidant species thallium(III), which is then available for reaction with other materials.

Accordingly, it is an object of the present invention to provide a method for producing a solution of thallium(III) from thallium(I) in a photoelectrochemical cell.

It is a further object to provide a photoelectrochemical system for producing thallium(III) wherein the reaction requires no source of energy other than solar radiation.

A still further object of the invention is to provide a process for utilizing photoelectrochemically generated thallium(III) in reactions with organic compounds.

These, and other important objects, will become more apparent from consideration of the following description and examples.

SUMMARY OF THE INVENTION

The present invention is directed to the photoelectrochemical production of thallium(III) in solution. A method for producing thallium(III) comprises (a) placing a solution containing thallium(I) in contact with a semiconductor photoelectrode and a counter electrode in a photoelectrochemical cell; (b) electrically interconnecting the photoelectrode and the counter electrode externally to the cell; and (c) generating a flow of current in the cell by exposing the photoelectrode to actinic radiation.

Alternatively, thallium(III) can be produced by (a) mixing a solution containing thallium(I) with a particulate semiconductor, (b) introducing oxygen into the mixture, and (c) exposing the mixture to actinic radiation.

The photoelectrochemically produced thallium(III) can be reacted with organic compounds which have an index of hydrogen deficiency greater than zero. Exemplary are thallium(III) reactions with compounds containing at least one carbon-carbon double bond, such as alkenes, cycloalkenes, alkenylarenes, alkyldienes, and cycloalkadienes, to form epoxides, carbonyl compounds and glycols or their esters.

Solutions of thallium(I) which can be used in the practice of the invention can be aqueous or nonaqueous.

DESCRIPTION OF THE INVENTION

The oxidation of thallium(I) to thallium(III) is accomplished in a photoelectrochemical cell having an externally electrically interconnected semiconductor photoelectrode and counter electrode.

In semiconductors, electronic orbitals are merged into bands of differing energy levels: a "valence band" which is nearly filled with electrons and a higher energy "conduction band" which is nearly vacant. The difference in energy between these bands is called the "band gap energy." A photon which strikes the surface of the semiconductor immersed in an electrolyte solution will, if its energy exceeds the semiconductor band gap energy, be absorbed and impart sufficient energy to a valence band electron so that it enters the conduction band, resulting in the formation of an electron-hole pair at the semiconductor surface and thereby giving rise to an electric field.

If the semiconductor is of the "n-type," that is, containing an electron donor species which causes some electrons to be in the conduction band, the electric field forms by electron shift toward the interior of the semiconductor and hole shift toward the surface.

A p-type semiconductor, on the other hand, contains electron acceptor species and forms electric fields in the opposite direction: holes shift into the semiconductor and electrons shift toward the surface.

The formed electric fields are unstable in conductive solutions and will rapidly disappear due to recombination of the electrons and holes, generally accompanied by the release of heat energy. However, if the electrolyte solution contains species which have suitable redox potentials (that is, intermediate between the semiconductor valence band and conduction band potentials), a photoelectrochemical cell can be formed by immersing an inert counter electrode in the electrolyte solution, and providing an electrical interconnection externally to the cell between the two electrodes. For an n-type semiconductor, irradiation of the semiconductor electrode now causes an electron flow toward the counter electrode, at which an available oxidized species can be reduced by accepting an electron while, essentially simultaneously, an available reduced species can be oxidized by transfer of an electron to the hole of the semiconductor electrode.

For a p-type semiconductor, processes at the two electrodes are reversed. The irradiated photoelectrode can transfer reducing electrons to an oxidized species, while available reduced species transfer electrons to the counter electrode, becoming oxidized.

As can be seen, the net result is a direct conversion of radiant energy to chemical species which can be stored or used for further chemical reactions. Light can be used to promote photooxidation at an n-type semiconductor photoelectrode, or to promote photoreduction at a p-type photoelectrode.

Factors which must be considered in the selection of a semiconductor for photoelectrochemical application include the theoretical energy conversion efficiency and the stability of the semiconductor material in the proposed system. As noted, electronic transitions in a photoelectrode require that the energy of the absorbed photon be greater than the semiconductor band gap energy. Solar radiation, however, is polychromatic, with most of its energy which is useful for chemical reactions reaching the surface of the earth at wavelengths between about 400 and about 900 nanometers (nm). Wrighton, in a paper entitled "Photochemistry," *Chemical and Engineering News,* Sept. 3, 1979, pages 29–47, (which is incorporated herein by this reference), has shown the theoretical efficiency for a range of wavelengths from infrared to ultraviolet, and describes a maximum efficiency of about 30 percent solar energy conversion at a wavelength of about 885 nm, equivalent to an energy of 1.4 electron volts (eV). For maximized solar energy efficiency, then, a semiconductor photoelectrode should have a band gap energy of about 1.4 eV.

The paper by Wrighton also discusses the stability problem which is exhibited by semiconducting photoanode materials, in that they are susceptible to oxidative decomposition when exposed to light. Only oxide semiconductors, e.g., ferric oxide or titanium dioxide, are described as useful in aqueous electrolytes without added stabilizers, but the band gap energies for these oxides (2.2 and 3.0 eV, respectively) do not permit efficient use of solar energy. Several photoanodes are available which have band gap energies at the ideal 1.4 eV level, but generally require nonaqueous electrolytes or the addition of electrode stabilizing agents.

For the previously noted thallium oxidation and oxygen reduction couples (Equations 1 and 4, respectively), it can be seen that the narrow 1.4 eV band gap should be energetically sufficient to generate a current flow. Assuming that the semiconductor material is not decomposed in the system, most of the currently used photoelectrode materials having band gap energies above about 1.4 eV are suitable for use in this invention. Several of these materials are tabulated by Wrighton in the previously noted paper at pages 37 and 43.

Typically, the choice of a semiconductor photoelectrode material will also be strongly influenced by the nature and energy requirements of the desired reaction at the counter electrode. For example, if thallium oxidation is to occur at a semiconductor photoanode and hydrogen evolution is desired at an inert cathode, according to Equation 12, the over-potential $$2H^+ + 2e^- \rightarrow H_2 \tag{12}$$

required to overcome the kinetic inefficiencies of the reaction will make necessary a larger band gap energy semiconductor than is predicted from standard reduction potentials. In addition, hydrogen evolution in systems utilizing a titanium dioxide photoanode requires the addition of a 0.2 volt bias potential in series with the photoelectrochemical cell, since the conduction band potential for this semiconductor is about 0.2 volts positive of the hydrogen evolution potential. The problem is discussed by Wrighton in "Photoelectrochemical Conversion of Optical Energy to Electricity and Fuels," in Accounts of Chemical Research, Vol. 12, pages 303-310 (1979), which is incorporated herein by this reference.

Numerous reactions can be made to occur at a counter electrode, including the reduction of oxygen (which concurrently results in the generation of electrical energy by the cell) and the electroreduction of organic compounds, as exemplified by the formation of hydrocarbons from carboxylic acids. The reduction of carbon dioxide to form alcohols and/or aldehydes can be performed at the cathode of a photoelectrochemical cell of this invention having a semiconductor photoanode.

It is also possible to practice the invention without a typical cell configuration having two electrodes. Thallium(III) is generated upon illumination of oxygen saturated solutions containing thallium(I) and a particulate semiconductor. Any particulate semiconductor which meets the above-described stability and energy criteria can be used in this modification of the invention, the theoretical explanation for operation of such "short-circuited" photoelectrochemical cells being explained by Bard in the previously noted paper from Science, at pages 142-143.

Since there are no electrodes in such a cell, it is not possible to apply bias potentials and, of course, there is no counter electrode reaction to be concerned with. This configuration, then, is useful primarily for the oxidation of thallium(I) and will not normally produce electrical energy or other products. It does offer the significant benefit of simplicity in both construction and operation of the cell.

In particulate semiconductor cells, oxygen saturation of the electrolyte is desired to maximum efficiency, but lower levels of dissolved oxygen can be utilized. Typically, this oxygen is supplied by bubbling the gas into the electrolyte. Mixtures of oxygen and other gases (e.g., air) can also be utilized in the practice of the invention.

The electrolyte used in the electrode or particulate-type cells comprises a suitable aqueous or organic solution containing sufficient ionic species to impart high conductivity. It is desirable that the ionic strength in the electrolyte be maintained above about 0.1 molar, for example from about 0.1 to about 10 molar, to facilitate rapid and efficient charge transfer to and/or from the semiconductor material.

Criteria to be utilized in selecting a solvent include the lack of significant reactivity toward thallium ions, capacity for dissolving a desired amount of thallium and ionizable species, and the ease with which reaction products can be separated. Many solvents known to the art of electrochemistry can be used, including water and diverse organic compounds, several of which are listed by J. O. Headridge in Electrochemical Techniques for Inorganic Chemists, page 68, Academic Press, New York (1969), which is incorporated herein by this reference. The organic solvents include such diverse compounds as acetonitrile, dimethylformamide, alcohols, and dimethyl sulfoxide. In addition, mixtures of water and miscible organic compounds, such as the water-acetic acidtetrahydrofuran solvent of Kruse in U.S. Pat. No. 3,641,067, are useful in the practice of the invention.

If water is used as the solvent, sufficient acid should be present so as to maintin a pH of less than about 2.5, to prevent hydrolysis of the photogenerated thallium-(III). However, if the system is designed such that thallium(III) is consumed by reaction as it is formed, the acid level requirement can be significantly decreased. Hydrolysis problems will be encountered to a much greater extent in high-pH systems where reaction of the thallium(III) occurs remotely in time or location from the photogeneration.

Ionic species in the electrolyte can be supplied by inorganic and organic salts which are highly ionized in solution, and are not reactive to any large extent with other components of the system. Mixtures of salts are also useful. Examples of these salts are perchlorates, acetates, sulfates, halides and the like. The cationic function of these salts can be alkali metals, hydrogen, ammonium, larger groups such as tetraethylammonium, and the like, including mixtures thereof.

In aqueous solutions at low pH, it has been found that the normally quite stable titanium dioxide photoelectrode is subject to degradation in the photooxidation of thallium, unless an electron transfer mediator such as acetate or sulfate ion is present in the electrolyte. A possible but not limiting chemical mechanism for the photooxidation is as follows in Equations 13 through 16, where $h_{vb}^+$ represents valence band holes and $e_{cb}^-$ represents conduction band electrons in the semiconductor:

$$TiO_2 \xrightarrow{light} h_{vb}^+ + e_{cb}^- \tag{13}$$

$$h_{vb}^+ + SO_4^{-2} \rightarrow .SO_4^- \tag{14}$$

$$.SO_4^- + Tl^+ \rightarrow SO_4^{-2} + Tl^{+2} \tag{15}$$

$$2Tl^{+2} \rightarrow Tl^+ + Tl^{+3} \tag{16}$$

Sulfate will mediate the reaction even when present at extremely low levels (e.g., less than about $10^{-7}$ molar) and is apparently not significantly consumed. In aqueous media, therefore, an electrolyte of aqueous sulfuric acid, from about 0.01 to about 5 molar, or a mixture of an inert salt (such as perchlorate) and a sulfate salt, would be beneficial.

Acetate, in the form of acetic acid or a salt, also mediates the reaction but is at least partially consumed via the previously noted photo-Kolbe reaction of Equation 11.

The invention is further illustrated by the following examples which are illustrative of various aspects of the invention, and are not intended as limiting the scope of the invention as defined by the appended claims.

EXAMPLE 1

The conversion of light to electrical energy is shown by operating a photoelectrochemical cell, based upon the thallium(I)-thallium(III) redox couple, in the photovoltaic mode.

A cell is constructed by placing a platinum wire counter electrode and an n-type single crystal semiconductor photoanode in a quartz beaker, and interconnecting the electrodes through an instrument for making electrical measurements. The semiconductor material is mounted in a Princeton Applied Research K0105 flat specimen holder, made of an inert polymer, which exposes a one square centimeter area of the material.

The electrodes are immersed in a stirred aqueous electrolyte solution which comprises 0.1 molar thallium(I) acetate, 0.1 molar thallium(III) perchlorate, and 0.5 molar acetic acid.

Upon irradiation of the photoanode with a xenon lamp, having an intensity of about 50 milliwatts per square centimeter (mW/cm$^2$), the following currents and voltages are obtained for several semiconductor materials:

| Semiconductor Material | Short-Circuit Photocurrent (mA/cm$^2$) | Open-Circuit Photovoltage (mV) |
|---|---|---|
| TiO$_2$ | 0.40 | 530 |
| MoS$_2$ | 1.2 | 190 |
| CdS | 2.3 | 800 |
| GaAs | 3.7 | 850 |

Stability of the photoelectrode is indicated by the maintenance of a short-circuit photocurrent for prolonged periods of time. Under illumination with a xenon light having an intensity of about 140 mW/cm$^2$, it is found that the electrode stability for the four semiconductor materials is an inverse function of the measured photocurrent. A titanium dioxide photoelectrode is the most stable, producing a short-circuit photocurrent of about 1.0 mA/cm$^2$ for more than eight hours, while the least stable gallium arsenide electrode photocurrent gradually declines from an initial 3 mA/cm$^2$ to about 1.8 mA/cm$^2$ in about sixty minutes, then sharply drops to about 0.25 mA/cm$^2$.

EXAMPLE 2

The efficiency of light conversion is determined using a photovoltaic cell, as in Example 1, but having an electrolyte solution comprising 1 molar thallium(I) acetate, 0.1 molar thallium(III) perchlorate, and 1 molar perchloric acid. Both unfiltered xenon light and light of a wavelength corresponding to the band gap energy of the photoelectrode (produced by narrow band pass interference filters over the xenon lamp) are used.

Efficiency of the conversion from thallium(I) to thallium(III) is calculated (as percent) by dividing the product of the cell photovoltage and 100 times the cell current (in mA/cm$^2$), by the light intensity (in mW/cm$^2$). A point of maximum efficiency can be determined by controlling the cell voltage with various reverse bias potentials, measuring cell current at each voltage, and plotting the calculated efficiencies versus cell voltage.

Using this technique, the following maximum efficiencies are obtained:

| Semiconductor Material | Light Wavelength | Intensity | Cell Volts | Maximum Efficiency, % |
|---|---|---|---|---|
| TiO$_2$ | 342 nm | 0.31 | 1.5 | 1.8 |
| TiO$_2$ | Xenon | 53 | 1.5 | 0.13 |
| MoS$_2$ | 700 nm | 0.62 | 0.8 | 0.6 |
| MoS$_2$ | Xenon | 50 | 0.62 | 0.017 |

EXAMPLE 3

This example demonstrates the photoelectrosynthetic generation of thallium(III) solutions.

A two-compartment cell, with a Vycor frit separating the compartments, is used for the experiment. The cathode compartment contains 0.5 molar acetic acid, is saturated with nitrogen, and is provided with a platinum wire cathode. The anode compartment has a quartz window for light transmission, and contains an electrolyte comprising 0.1 molar thallium(I) acetate and 0.5 molar acetic acid. An n-type single crystal titanium dioxide photoanode, mounted as described in Example 1, is placed into the anode compartment behind the quartz window. A reference potential for measurements is provided by a Princeton Applied Research K0077 saturated calomel electrode, placed in the anode compartment of the cell. The three electrodes are connected to a Princeton Applied Research 173D Potentiostat.

Under illumination with a xenon lamp producing an intensity of about 52 mW/cm$^2$, thallium(I) oxidation at the photoanode begins at a potential of $-0.2$ volts versus the reference electrode. With no light, the oxidation is initiated at a platinum electrode inserted into the anode compartment with an applied potential of $+0.6$ volts versus the reference electrode. The difference between these potentials, 0.8 volts, represents the energy which is supplied by light.

With the potentiostat used to maintain a photoanode potential of $+0.4$ volts (versus the reference electrode), and with an illumination intensity of about 140 mW/cm$^2$, thallium(III) is produced at a rate of 0.058 millimoles per hour, as measured both spectrophotometrically by absorbance at 260 nm and also by polarographic analysis. Under these conditions, hydrogen is produced at the cathode.

A thin film titanium dioxide photoelectrode is prepared by heating a piece of titanium foil in air at about 700° C. for about two hours, and then continuing the heating in an atmosphere of hydrogen sulfide for about one hour. With this electrode substituted for the single crystal in the electrode holder, repeating the experiment of the preceding paragraph results in a similar production rate of thallium(III), as shown below:

| Species Produced | 10$^{-3}$ Equivalents/Hour |
|---|---|
| Coulombs | 0.039 ± 0.001 |
| Thallium(III) | 0.041 ± 0.002 |
| Hydrogen | 0.043 ± 0.002 |

It should be noted that the current efficiency is approximately 100 percent, indicating that there are no other products, i.e., no photooxidation of water.

EXAMPLE 4

The photoelectrosynthetic generation of thallium-(III) is further demonstrated, using a photoanode of a different semiconductor material.

Experiments of the preceding example are repeated with the same cell configuration and solutions, but with an n-type single crystal molybdenum disulfide photoanode, mounted as previously described. All tests for this example using illumination employ the xenon lamp operating at an intensity of about 52 mW/cm$^2$.

Without illumination, an applied potential of +0.6 volts versus the reference electrode (as reported in the preceding example) is required to initiate the oxidation of thallium(I). Under illumination, the oxidation using the molybdenum disulfide photoanode begins at about +0.3 volt versus the reference electrode, giving an "underpotential" of about 0.3 volts.

By controlling the cell potential at +0.7 volts versus the reference electrode, the illuminated photoanode produces thallium(III) at the rate of about 0.00083 millimoles per hour.

EXAMPLE 5

Thallium(III) is generated with a photoelectrochemical cell using a nonaqueous electrolyte.

A cell constructed as in Example 1 is operated with an electrolyte comprising a solution of 0.1 molar thallium(I) acetate and 0.1 molar thallium(III) nitrate in acetonitrile. With illumination from a xenon lamp of about 50 mW/cm$^2$ intensity on a single crystal n-type titanium dioxide photoanode, a short-circuit current of 0.13 mA/cm$^2$ and an open-circuit photovoltage of about 0.9 volts are obtained. The maximum energy conversion efficiency of the cell is about 0.0048 percent.

Similarly, using the same cell illumination and electrolyte, but with a single crystal molybdenum disulfide photoanode, a short-circuit current of 0.085 mA/cm$^2$ and an open-circuit photovoltage of 0.21 volts are found. This cell has a maximum conversion efficiency of about 0.014 percent.

EXAMPLE 6

The effect of an electron transport mediator upon the stability of a photoelectrode is demonstrated.

A photoelectrochemical cell is constructed in a quartz beaker, as described in preceding examples, using a platinum-wire cathode and a thin-film titanium dioxide photoanode (prepared as described in Example 3), with an aqueous electrolyte solution of 0.1 molar thallium(I) perchlorate, 1 molar sodium perchlorate, and sufficient perchloric acid to obtain a pH of about 2.6. The potentiostat is used to maintain a photoanode potential of 0.4 volts versus a saturated calomel electrode, and the photoanode is illuminated with a xenon lamp operated at an intensity of about 140 mW/cm$^2$.

Initially, the cell current is 0.15 mA/cm$^2$, but this decreases to zero during operation, with a half-life of about one minute. The photoelectrode is destroyed, as evidenced by a large dark current.

When the experiment is repeated using a replacement photoanode, and with sodium sulfate added to the electrolyte to a concentration of about 10$^{-7}$ molar, an initial cell current of 0.3 mA/cm$^2$ is stable for at least 24 hours. Since many more moles of thallium(III) are produced than the moles of sulfate present, it does not appear that sulfate is consumed during the photooxidation.

The thin-film titanium dioxide used in the acetate electrolyte experiment of Example 3 yields a current of 0.3 mA/cm$^2$ which is stable for at least 22 hours. However, some carbon dioxide is evolved, indicating the possibility that acetate ion is being consumed via the photo-Kolbe reaction.

EXAMPLE 7

Thallium(III) is produced by photooxidation in a cell using semiconductor powders.

A quartz beaker containing 250 milliliters of an aqueous solution, which is 0.1 molar thallium(I) acetate and 0.5 molar acetic acid, and 1.0 gram of semiconductor powder is saturated with oxygen by bubbling the gas through the solution. The beaker is illuminated with a xenon lamp having an intensity of about 140 mW/cm$^2$, and the production of thallium(III) is monitored by a spectrophotometric measurement of the increase in absorbance at a wavelength of 260 nm. Results are as shown below for several semiconductors:

| Semiconductor | | Thallium(III) Production |
| --- | --- | --- |
| Type | Band Gap (eV) | 10$^{-3}$ Molar/Hour |
| TiO$_2$ (platinized) | 3.2 | 0.55 |
| TiO$_2$ | 3.2 | 0.53 |
| ZnO | 3.2 | 0.27 |
| WO$_3$ (H$_2$ reduced) | 2.8 | 0.14 |
| WO$_3$ | 2.8 | 0.13 |
| Ho$_2$O$_3$ | 2.8 | 0.043 |
| SiC | 2.2 | 0.024 |
| Y$_2$O$_3$ | — | 0.017 |
| Ce$_2$(WO$_4$)$_3$ | — | 0.0072 |
| Si$_3$N$_4$ | — | <0.0001 |
| RuO$_2$ | — | <0.0001 |

EXAMPLE 8

A photoelectrochemical process is used to generate thallium(III), which is reacted with an olefin and then regenerated.

Into a 500-milliliter flask is placed 250 milliliters of an aqueous solution of 0.1 molar thallium(I) acetate and 0.5 molar acetic acid. A 2.0 gram portion of powdered titanium dioxide is added to the flask, and oxygen is bubbled through the solution. A xenon lamp illuminates the flask with an intensity of about 140 mW/cm$^2$, and polarographic analysis is used to monitor the production of thallium(III), with results as follows:

| Elapsed Time (hours) | Thallium(III) (molar) |
| --- | --- |
| 0 | <2.5 × 10$^{-5}$ |
| 3 | 1.6 × 10$^{-3}$ |
| 5 | 2.2 × 10$^{-3}$ |
| 21 | 3.6 × 10$^{-3}$ |

The flask is removed to a hot water bath, maintained at 85° C., and propylene (humidified by bubbling through a heated 0.5 molar acetic acid solution) is bubbled through the solution. Gases exiting the flask are passed through a first collection flask maintained at about 0° C. (in an ice bath) and then through a second collection flask at about −78° C. (in an isopropyl alcohol-dry ice bath).

After about 1.5 hours, propylene flow is stopped, and polarographic analysis of the solution indicates a thallium(III) concentration of 2.9×10$^{-5}$ molar. Contents of the collection flasks are identified by gas chromatography as acetone and propylene oxide, in approximately a 4:1 molar ratio.

Oxygen is again bubbled into the solution and illumination is resumed, giving thallium(III) production as follows:

| Elapsed Time (hours) | Thallium(III) (molar) |
| --- | --- |
| 0 | $2.9 \times 10^{-5}$ |
| 3 | $1.5 \times 10^{-3}$ |
| 5 | $2.1 \times 10^{-3}$ |
| 21 | $3.6 \times 10^{-3}$ |

Repeating the propylene oxidation experiment reduces the thallium(III) concentration to $3.2 \times 10^{-4}$ molar, and the subsequent thallium(III) photoelectrochemical regeneration step proceeds as follows:

| Elapsed Time (hours) | Thallium(III) (molar) |
| --- | --- |
| 0 | $3.2 \times 10^{-4}$ |
| 3 | $1.7 \times 10^{-3}$ |
| 5 | $2.1 \times 10^{-3}$ |
| 21 | $3.6 \times 10^{-3}$ |

The produced thallium(III) remains reactive to propylene, as shown by the decrease in concentration to $3.7 \times 10^{-5}$ molar when the propylene oxidation experiment is again repeated.

Various embodiments, and modifications of this invention, have been described in the foregoing description and examples, and further modifications will be apparent to those skilled in the art. Such modifications are included within the scope of the invention as defined by the following claims.

We claim:

1. A method for producing thallium(III) in solution which comprises:
    (a) placing a solution containing thallium(I) into a photoelectrochemical cell fitted with a semiconductor photoelectrode and a counter electrode, said photoelectrode and counter electrode having an electrical interconnection external to said cell; and
    (b) exposing said photoelectrode to actinic radiation, generating a flow of current in said cell.

2. The method defined in claim 1 wherein said solution is aqueous.

3. The method defined in claim 1 wherein said solution is nonaqueous.

4. The method defined in claim 1 wherein said solution contains sufficient dissolved substances to yield an ionic strength of at least about 0.1 molar.

5. The method defined in claim 1 wherein said cell is divided into two compartments.

6. The method defined in claim 1 wherein said radiation is solar radiation.

7. The method defined in claim 1 wherein said photoelectrode is a photoanode.

8. The method defined in claim 7 wherein said photoanode comprises titanium dioxide.

9. The method defined in claim 8 wherein an electron transfer mediator is present in said solution.

10. The method defined in claim 9 wherein said electron transfer mediator is sulfate ion.

11. The method defined in claim 8 wherein an electrical bias of at least 0.2 volts is applied in series with said cell, and hydrogen gas is evolved at said counter electrode, concurrently with thallium(III) production.

12. The method defined in claim 7 wherein an oxygen-containing gas is supplied to said counter electrode, and electricity is generated through a load inserted into said electrical interconnection, concurrently with thallium(III) production.

13. The method defined in claim 7 wherein carbon-containing compounds are reduced at said counter electrode, concurrently with thallium(III) production.

14. A method for producing thallium(III) in solution which comprises:
    (a) mixing a solution containing thallium(I) with a particulate semiconductor;
    (b) introducing an oxygen-containing gas into said mixture; and
    (c) exposing said mixture to actinic radiation.

15. The method defined in claim 14 wherein said solution is aqueous.

16. The method defined in claim 14 wherein said solution is nonaqueous.

17. The method defined in claim 14 wherein said solution contains sufficient dissolved substances to yield an ionic strength of at least about 0.1 molar.

18. The method defined in claim 14 wherein said semiconductor is of the n-type.

19. The method defined in claim 14 wherein said radiation is solar radiation.

20. A method for oxidizing organic compounds which comprises:
    (a) placing a solution containing thallium(I) into a photoelectrochemical cell fitted with a semiconductor photoelectrode and a counter electrode, said photoelectrode and counter electrode having an electrical interconnection external to said cell;
    (b) exposing said photoelectrode to actinic radiation, generating a flow of current in said cell and producing a solution containing thallium(III); and
    (c) reacting said thallium(III) with an organic compound having an index of hydrogen deficiency greater than zero.

21. The method defined in claim 20 wherein said radiation is solar radiation.

22. The method defined in claim 20 wherein said photoelectrode is a photoanode.

23. The method defined in claim 22 wherein said photoanode comprises titanium dioxide.

24. The method defined in claim 23 wherein an electrical bias of at least about 0.2 volts is applied in series with said cell, and hydrogen gas is evolved at said counter electrode, concurrently with thallium(III) production.

25. The method defined in claim 22 wherein an oxygen-containing gas is supplied to said counter electrode, and electricity is generated through a load inserted into said electrical interconnection, concurrently with thallium(III) production.

26. The method defined in claim 20 wherein said organic compound is selected from the group consisting of unsaturated compounds, cyclic compounds, and mixtures thereof.

27. The method defined in claim 26 wherein said organic compound is one or more selected from the group consisting of alkenes, cycloalkenes, alkenylarenes, alkyldienes, aromatics, and cycloalkadienes, and wherein the product of reaction with said thallium(III) comprises one or more components selected from the group consisting of epoxides, carbonyl compounds, glycols, and glycol esters.

28. A method for oxidizing organic compounds which comprises:
   (a) mixing a solution containing thallium(I) with a particulate semiconductor;
   (b) introducing an oxygen-containing gas into said mixture;
   (c) exposing said mixture to actinic radiation, producing a solution containing thallium(III): and
   (d) reacting said thallium(III) with an organic compound having an index of hydrogen deficiency greater than zero.

29. The method defined in claim 28 wherein said radiation is solar radiation.

30. The method defined in claim 28 wherein said organic compound is selected from the group consisting of unsaturated compounds, cyclic compounds, and mixtures thereof.

31. The method defined in claim 30 wherein said organic compound is one or more selected from the group consisting of alkenes, cycloalkenes, alkenylarenes, alkyldienes, aromatics, and cycloalkadienes, and wherein the product of reaction with said thallium(III) comprises one or more selected from the group consisting of epoxides, carbonyl compounds, glycols, and glycol esters.

32. A method for producing epoxides which comprises:
   (a) placing a solution containing thallium(I) into a photoelectrochemical cell fitted with a semiconductor photoanode and a counter electrode, said photoanode and counter electrode having an electrical interconnection external to said cell;
   (b) exposing said photoanode to actinic radiation, generating a flow of current in said cell and producing thallium(III): and
   (c) reacting said thallium(III) with a compound selected from the group consisting of alkenes, cycloalkenes, alkenylarenes, alkyldienes, aromatics, and cycloalkadienes.

33. The method defined in claim 32 wherein said radiation is solar radiation.

34. A method for producing epoxides which comprises:
   (a) mixing a solution containing thallium(I) with a particulate semiconductor;
   (b) introducing an oxygen-containing gas into said mixture;
   (c) exposing said mixture to actinic radiation, producing a solution containing thallium(III): and
   (d) reacting said thallium(III) with a compound selected from the group consisting of alkenes, cycloalkenes, alkenylarenes, alkyldienes, aromatics, and cycloalkadienes.

35. The method defined in claim 34 wherein said radiation is solar radiation.

* * * * *